United States Patent [19]

Sekine et al.

[11] Patent Number: 5,577,999
[45] Date of Patent: Nov. 26, 1996

[54] ORTHOPAEDIC SUPPORTER KIT

[75] Inventors: Takayuki Sekine, Kawaguchi; Hiroshi Yamaguchi, Tokyo, both of Japan

[73] Assignee: Alcare, Co. Ltd., Tokyo, Japan

[21] Appl. No.: 425,956

[22] Filed: Apr. 19, 1995

[30] Foreign Application Priority Data

Apr. 20, 1994 [JP] Japan .................... 6-106095

[51] Int. Cl.$^6$ ........................... A61F 5/04
[52] U.S. Cl. ..................... 602/8; 602/5; 602/6
[58] Field of Search ............... 602/5, 6, 8, 9, 602/60, 63, 77; 128/856, 877, 878; 604/368, 369, 378

[56] References Cited

U.S. PATENT DOCUMENTS

| | | |
|---|---|---|
| 4,376,438 | 3/1983 | Straube et al. . |
| 4,433,680 | 2/1984 | Yoon . |
| 4,499,896 | 2/1985 | Heinecke ........................... 602/65 |
| 4,574,793 | 3/1986 | Lee et al. . |
| 4,628,917 | 12/1986 | Campagna, Jr. et al. ........... 602/8 |
| 4,638,795 | 1/1987 | Richter et al. . |
| 4,667,661 | 5/1987 | Scholz et al. . |
| 4,690,842 | 9/1987 | Kammerer et al. . |
| 4,856,502 | 8/1989 | Ersfeld et al. . |
| 4,888,225 | 12/1989 | Sandvig et al. .................... 602/8 X |
| 4,899,738 | 2/1990 | Parker .................................. 602/8 |
| 4,934,356 | 6/1990 | Klintworth, Jr. ..................... 602/8 |
| 5,027,803 | 7/1991 | Scholz et al. ....................... 602/8 |
| 5,176,621 | 1/1993 | Shulz ................................... 602/8 |
| 5,324,252 | 6/1994 | Libbey et al. ..................... 602/8 X |

FOREIGN PATENT DOCUMENTS

| | | |
|---|---|---|
| 59-13216 | 3/1984 | Japan . |
| 61-41465 | 2/1986 | Japan . |
| 1-175854 | 7/1989 | Japan . |
| WO89/08463 | 9/1989 | WIPO . |

OTHER PUBLICATIONS

English Summary of Japanese Examined Patent Application Publication No. Sho 59–13216.
English Summary of Japanese Unexamined Patent Application Publication No. Sho 61–41465.
English Summary of Japanese Unexamined Patent Application Publication No. Hei 1–175854.

Primary Examiner—Richard J. Apley
Assistant Examiner—Kim M. Lee
Attorney, Agent, or Firm—Haverstock, Garrett & Roberts

[57] ABSTRACT

An orthopaedic supporter kit comprises a fixing member including a main fixing body enclosed within a moisture-impermeable container, the main fixing body including a support body made of a flexible base material impregnated with a water curable resin, the support body having an outer surface and an opposite inner surface, and a covering member covering the outer surface of the support body and bondable to the curable resin, a cushioning member formed of a relatively elastic and bulky material, the cushioning member having an outer surface, an opposite inner surface, and opposite side end portions, the cushioning member being adapted to be positioned around a diseased part of a patient's body and conformed to the shape of the diseased part with the inner surface of the cushioning member directly applied to the diseased part and the opposite side end portions positioned in adjacent relation so as to be capable of being adjustably coupled together by fasteners, and fasteners for adjustably coupling together the side end portions of the cushioning member, wherein the main fixing body can be removed from within the moisture-impermeable container and contacted with water, the inner surface of the support body brought into contact with the outer surface of the cushioning member and, in this state, left to cure, whereby the support body, the covering member and the cushioning member of the main fixing body can be rendered into one integral structure which is adjustably fixable to the diseased body part and easily removable and replaceable thereon.

20 Claims, 2 Drawing Sheets

ORTHOPAEDIC SUPPORTER KIT

INDUSTRIAL FIELD OF UTILIZATION

The present invention relates to an orthopaedic supporter kit which is placed or mounted on a diseased or injured part of a patient's body so as to fix and support the diseased part for the purpose of treating a bone fracture, a sprain, a dislocation or the like, or protecting such affected part.

PRIOR ART

In the field of orthopaedic therapy, emergency treatment, etc., there are known various methods for fixing and supporting diseased and injured parts of a patient's body by mounting or placing an orthopedic supporter over the diseased part for such purposes as treating a bone fracture, a sprain, a dislocation or the like or protecting such affected part. More concretely, there are known methods wherein a material such as wood, plastics, metal or the like is worked or processed so as to conform to the shape of the diseased part of a patient's body, a cotton bandage or the like is wound around the thus processed material, and the resulting product is applied onto the diseased part, around which a bandage is further wound for fixation. According to another known method, a thermoplastic resin sheet is cut and processed so as to fit over the diseased part, a cushioning material is attached to the skin-side surface of the thus processed thermoplastic sheet, and the thus obtained product is mounted on the diseased part by use of a fixing member such as a cord. According to still another known method, a flexible base material impregnated with a water-curable resin is applied to the diseased part, so that, by allowing the water-curable resin to cure, the base material is hardened. In the case of the first method discussed above, time and skill are required for the processing of the material, and moreover, the fixation of the thus obtained orthopaedic supporter must be effected by winding a bandage thereon turn by turn; and thus, the mounting and demounting of the orthopaedic supporter are very troublesome. Further, the adjustment of the fixing force acting on the respective portions of the thus mounted orthopaedic supporter is almost impossible. In the case of the second method, the use of a high-level casting technique and heating means is required for processing the thermosetting plastic sheet, and the mounting or demounting of the orthopaedic supporter cannot be performed easily, and moreover, the fixing force is hard to adjust. In the case of the third method, although the base material can be easily formed so as to conform to the diseased part, it is troublesome to mount or demount the base material once it cures, and the fixing force cannot be easily adjusted.

SUMMARY OF THE INVENTION

Problems That The Invention Is To Solve

It is an object of the present invention to provide an orthopaedic support member constructed in such a manner that the orthopaedic supporter can be easily formed in conformity with the shape of the injured or diseased part of a patient's body, the mounting or demounting thereof can be easily carried out, and in addition, the fixing force thereof can be easily adjusted.

Means Of Solving The Problems

In order to achieve the above-mentioned object, the orthopaedic supporter kit according to the present invention includes in combination a fixing member which is curable and hardenable after contact with water and forms the outer portion of the supporter; and a cushioning member which locates between the fixing member and the diseased body part and includes means enabling adjusting the fixing force and removably mounting the supporter on the diseased body part.

The preferred fixing member is constituted in such a manner that a main fixing body is hermetically enclosed within a moisture-impermeable container. The main fixing body includes a support body made of a flexible base material impregnated with a curable resin which cures upon contact with water. A covering member covers the outer surface of the support body and is bondable to the curable resin. A separable surface protective member covers the inner surface of the support body. The preferred cushioning member is composed of an elastic and bulky material in which rifts or slits can be formed. Fasteners, such as the hook portion of hook-and-loop fasteners, are attachable to the outer surface of the cushioning member. The cushioning member has an inner surface which can be directly applied to the diseased part of a patient's body, and two side end portions. The two side end portions of the outer surface of the cushioning member can be coupled together by means of the hook-and-loop fasteners, whereby the cushioning member can be detachably fixed to the diseased body part.

Operation Of The Invention

According to the preferred embodiment of the present invention, the cushioning member is wrapped, placed or mounted around the diseased or injured part of a patient's body in such a manner that the inner surface of the cushioning member is contacted with the diseased body part, and the side end portions of the outer surface of the cushioning member are positioned in adjacent relation so as to be capable of being joined to each to other by use of the hook portions of hook-and-loop fasteners, whereby the cushioning member is fixed to the diseased body part. The hermetically sealed container in which the fixing member is contained is opened, and the fixing member is taken out from the container. The fixing member thus taken out is immersed in or otherwise contacted with water sufficiently so as to absorb a suitable amount of water. Subsequently, the fixing member is pressed against the outer surface of the cushioning member in such a manner that the inner surface of the support body with the surface protective member removed therefrom is contacted with the outer surface of the cushioning member. During this period, the curing of the water-curable resin with which the support body is impregnated proceeds, as a result of which the thus cured support body and the cushioning and the covering members lying on both sides of said support body are rendered into one integral structure. By adjusting the attachment of the respective hook fasteners to the outer surface of the cushioning member so as to tighten or loosen the cushioning member about the diseased body part, the fixing force or compression of the diseased body part at intervals along the length of the supporter can be adjusted. Also, by unfastening the fasteners, the main fixing body can be removed from the diseased part together with the cushioning member.

BRIEF DESCRIPTION OF THE DRAWINGS

FIGS. 1a–1d show the components of a preferred embodiment of an orthopaedic supporter kit according to the present invention, wherein: FIG. 1a shows a sectional view of a fixing member according to the present invention contained in a hermetically sealed container; FIGS. 1b and 1c respectively show a sectional view and a plan view of a cushioning member according to the present invention; and FIG. 1d shows a plan view of a typical hook portion of a hook-and-loop fastener used with the cushioning member of FIGS. 1b and 1c.

FIGS. 2a–2j illustrate preparation and application of the supporter for fixation of the lower leg of a patient, wherein: FIG. 2a is a plan view of the cushioning member of FIGS. 1b and 1c; FIG. 2b is a perspective view showing application of the cushioning member to a patient's lower leg portion; FIG. 2c is a perspective view showing the cushioning member in position on the lower leg of FIG. 2b; FIG. 2d is a perspective view of the hermetically sealed container of FIG. 1a, showing removal of the fixing member therefrom; FIG. 2e is an elevational view illustrating immersion of the fixing member in water; FIG. 2f is a perspective view of the fixing member showing removal of the surface protective material; FIG. 2g is a side view of the lower leg and cushioning member of FIG. 2c showing the fixing member being modeled thereon; FIG. 2h is a side view of the lower leg showing an elastic bandage wound about the supporter to shape it; FIG. 2i is a side view of the lower leg showing the finished supporter thereon; and FIG. 2j is a representative cross-sectional view of the finished supporter of FIG. 2i.

DETAILED DESCRIPTION OF THE PREFERRED EMBODIMENT

A preferred embodiment of the present invention will now be described by reference to the drawings.

Figure 1A:
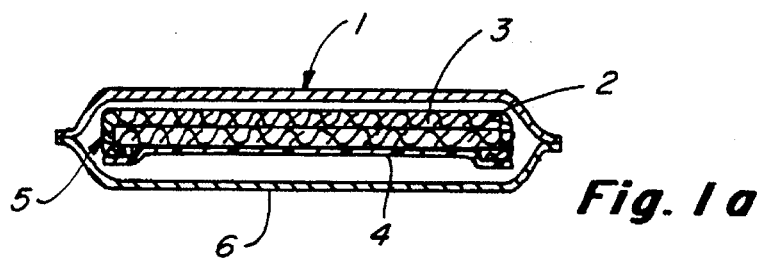

FIG. 1a is a sectional view of a fixing member 1, wherein a main fixing body 5 is housed in a hermetically sealed container 6 which is composed of a moisture-impermeable material and filled with an inert gas. The main fixing body 5 includes a support body 2 composed of an elastic base material impregnated with a water-curable resin which cures upon contact with water; a covering member 3 which covers that surface of the support body 2 which lies on the outside when the orthopaedic supporter is mounted on an injured or diseased part of a patient's body; and a surface protective material 4 covering the opposite surface of the support body 2, that is, the surface which lies on the inner side facing the diseased body part when the orthopaedic supporter is mounted thereon.

Figure 1B:
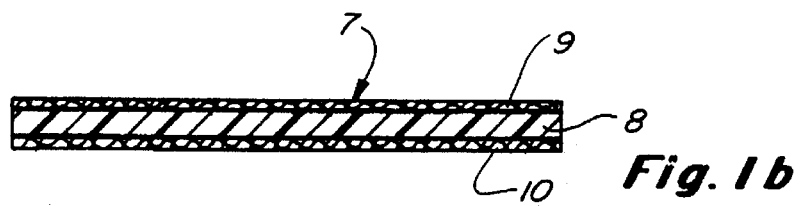
Figure 1C:
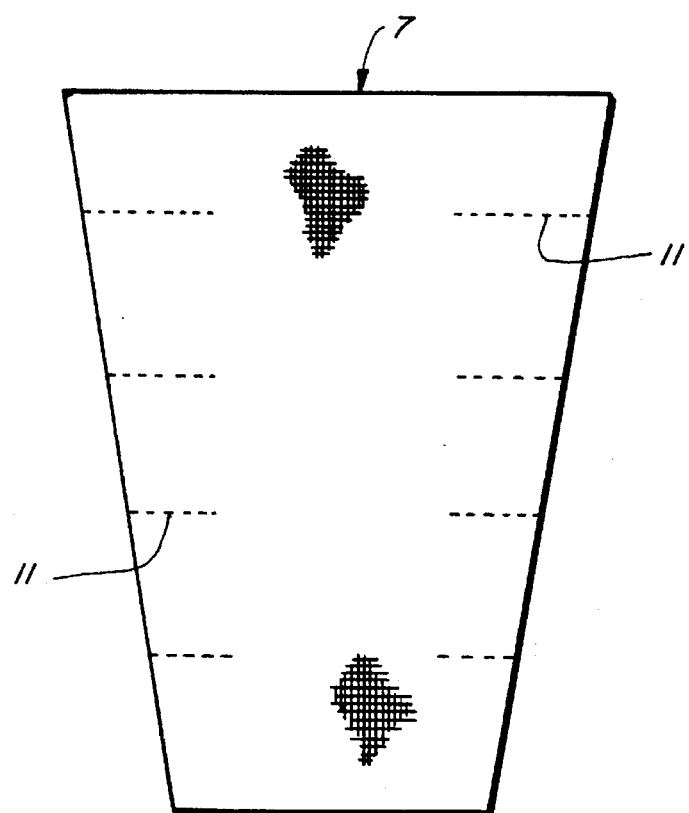

FIG. 1b shows a sectional view of a cushioning member 7, and FIG. 1c shows a plan view of the cushioning member 7. The cushioning member 7 includes a core material 8 covered with a front surface material 9 which lies on that side of the core material 8 which is on the outside when the orthopaedic supporter is mounted on the diseased part of a patient's body, and a rear surface member 10 which lies on the surface of the diseased part of the patient's body when the orthopaedic supporter is mounted thereon. In the cushioning member 7, rifts or slits 11, as shown in broken lines, can be provided depending on the part of the patient's body onto which the orthopaedic supporter is to be applied.

Figure 1D:
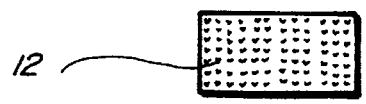

FIG. 1d shows a plan view of the hook portion of a hook-and-loop type fastener 12 of conventional construction.

Figure 2A:
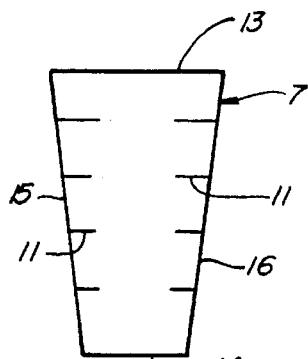
Figure 2B:
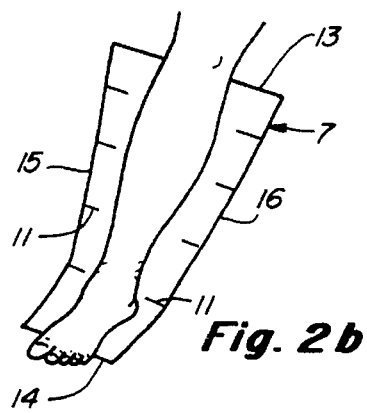
Figure 2C:
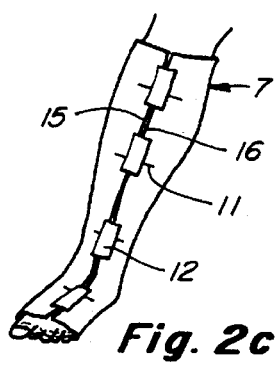

Next, the actual use of the orthopaedic supporter according to the present invention will be described by reference to FIGS. 2a–j, which show, as an example, the orthopaedic supporter of FIGS. 1a–1d applied to a bone fracture in a lower leg of a patient. First, the cushioning member 7 is prepared as shown in FIG. 2a. The cushioning member 7 is cut into a slender tapered shape in such a manner that its width becomes narrower from an upper end 13 to a lower end 14 thereof, and, in the cushioning member 7, a plurality of slits 11 are provided in its width direction. Subsequently, the cushioning member 7 is applied to the lower leg in such a manner that, as shown in FIG. 2b, the upper end 13 which has the largest width is located on the calf portion of the lower leg, and, in this state, the part of the patient's leg which extends from the rear lower leg portion to the sole of the foot is wrapped up in the cushioning member 7, and then, as shown in FIG. 2c, side ends 15 and 16 of the cushioning member 7 are brought around to the front side of the lower leg and coupled together by use of hook fasteners 12, whereby the cushioning member 7 is fixed to the lower leg portion of the patient.

Figure 2D:
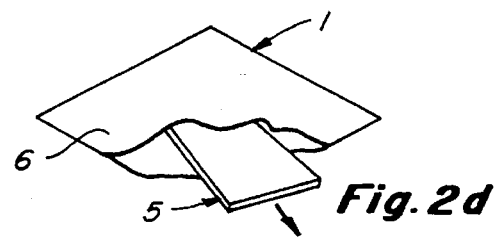
Figure 2E:
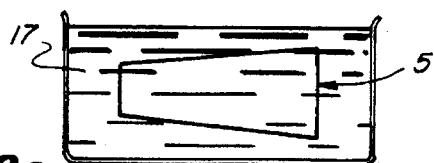
Figure 2F:
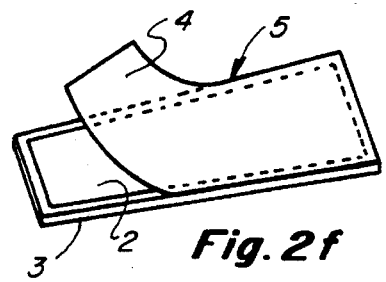
Figure 2G:
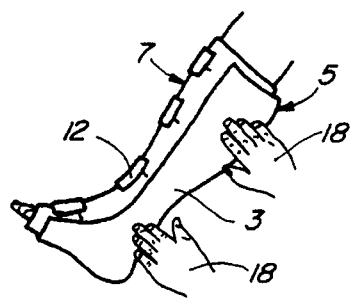
Figure 2H:
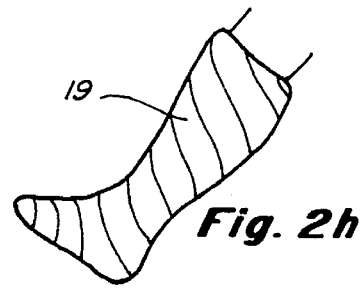
Figure 2I:
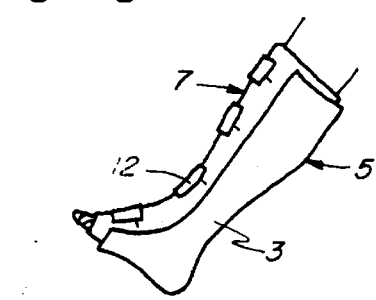
Figure 2J:
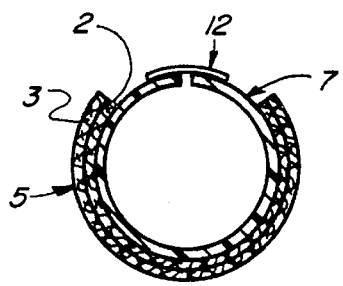

Then the container 6 containing the fixing member 1 is opened, and the main fixing body 5 housed therein is taken out as shown in FIG. 2d; subsequently, the main fixing body 5 is dipped into water 17, as shown in FIG. 2e, so as to absorb a suitable amount of water; the surface protective member 4 is removed from the support body 2 as shown in FIG. 2f; thus the exposed inner surface of the support body 2 is applied, as shown in FIG. 2g, onto that portion of the rear outer surface of the cushioning member 7 which extends from the rear lower leg portion to the sole of the foot; and a modeling operation is performed with hands 18 by manipulating the covering material 3 of the main fixing body 5 so that the main fixing body 5 is conformed to the shape of the underlying portion of the lower leg. Next, as shown in FIG. 2h, on the main fixing body 5 and the cushioning member 7, a member 19 such as an elastic bandage is wound and left in a fixedly wound state for about 10 minutes, as a result of which the water-curable resin of the support body 2 cures, so that the inner surface of the support body 2 and the outer surface of the cushioning member 7 fixedly adhere to each other. Subsequently, the elastic bandage 19 is removed, whereby a structure in which the main fixing member 5 and the cushioning member 7 are rendered into one integral structure is obtained as shown in FIG. 2i. FIG. 2j shows a sectional view of the resulting structure. By adjusting and refastening side ends 15 and 16 of the cushioning member 7 together by use of the hook fasteners 12, the compressive force acting against the lower leg portion, that is, the fixing force of the corresponding portions of the cushioning member 7 on the lower leg, can be adjusted. Further, if the hook fasteners 12 are removed, the front portion of the cushioning member 7 can be opened, so that the cushioning member 7 and the main fixing body 5 can be removed from the patient's leg.

The base material which constitutes the support body 2 of the main fixing body 5 can be any suitable material that is relatively bulky and non-reactive with the resin, receives the resin well and is flexible. As the base material, natural fiber, artificial fiber (such as inorganic fiber, regenerated artificial fiber, semi-synthetic fiber or synthetic fiber) or a combination of these fibers can be used. As for the fibrous structure of the base material, a so-called cubic knit or knitted fabric comprising a three-layer structure consisting of a surface fabric; a bottom fabric; and a jointing portion consisting of threads extending between the surface and bottom fabrics is advantageously used. For instance, for the surface fabric and the bottom fabric, polyester threads of 250 denier are used, respectively, in the form of a warp knit or knitted fabric of 14.5 per inch in the wales direction and 23 per inch in the course direction, and as the jointing threads, polyester threads of 300 denier should desirably be used, and the finished thickness should desirably be set at from about 1 to about 10 mm.

The desirable properties required of the curable resin with which the base material is impregnated are as follows: the curable resin should be curing-reactive with water, unstimulative and safe to the human body, have excellent storage stability and have a viscosity of about 18,000 to about 50,000 cps at room temperature and a curing time of about 2 to about 30 minutes at room temperature. The curable resin used in the present invention can contain a prepolymer, a catalyst, a stabilizer, an anti-foaming or defoaming agent, an antioxidant, etc.

As an example of a suitable prepolymer, there can be used a polyol (such as for instance a polyethylene glycol, a polypropylene glycol, a polyester polyol, a polycaprolaction diol, a polyoxyethylenesorbitan ester, an ethoxylated castor oil or the like), or, a polyisocyanate (such as for instance 4,4'-diphenylmethane diisocyanate, methylene-bis (4-cyclohexyl isocyanate), 5'-naphthalene diisocyanate, xylene diisocyanate, tolylene diisocyanate, or hexamethylene diisocyanate). As the catalyst, there can be used a tertiary amine (such as for instance a morpholine system substance (such as for instance 4 -{2-(1-methyl-2-(4-morphonyl) ethoxy-)ethyl}-morpholine (MEMPE), dimorpholinodiethylether, or bis (2,6-dimethylmorpholino) diethylether), or bis (dimethylaminoethyl) ether or the like). As the stabilizer, there can be used an organic acid (such as for instance methanesulfonic acid, ethansulfonic acid). As the defoaming agent, a siloxane copolymer (such as for instance polydimethylsiloxane or a modified substance thereof or the like). As the anti-oxidant, for instance tetrakis [methylene-3-(3',5 ditertiary-butyl-4-hydroxyphenyl)propionate]methane. Further, there can be used various other substances which have so far been used as conventional water-curable cast materials. They are disclosed in Japanese Unexamined Patent Application Publication No. Sho 53-*61184*, Japanese Unexamined Patent Application Publication No. Sho 58-*146351*, Japanese Examined Patent Application Publication No. Sho 59-13216, Japanese Unexamined Patent Application Publication No. Sho 61-41465, Japanese Unexamined Patent Application Publication No. Sho 61-37165, Japanese Unexamined Patent Application Publication No. Sho 62-172008, Japanese Unexamined Patent Application Publication No. Sho 62-87162, Japanese Unexamined Application Publication No. Sho 63-286152, Japanese Unexamined Patent Application Publication No. Sho 63-197461, Japanese Unexamined Patent Application Publication No. Hei 1-175854, and Japanese Unexamined Patent Application Publication No. Hei 3-503611.

The necessary conditions required of the covering material of the main fixing body are as follows: the covering material must be non-reactive with the resin, bondable to the resin, high in air permeability, low in water absorption, and flexible (stretchable with a low modulus). Further, the covering material should desirably be of such a size that it can cover at least the whole of the outer surface of the support body and, further, a part of the peripheral portion of the inner surface (that is, the surface on which the surface protective material is provided) of the support body. As the material of the covering member, either artificial fiber or natural fiber can be used, for instance, polyester is a preferable material. A non-woven polyester fabric which has a weight of about 68 g/m$^2$, a maximum lengthwise stretch ratio of about 45% and a maximum widthwise stretch ratio of about 120% can be used advantageously. This non-woven fabric can be obtained by use of any of several conventional manufacturing methods such as a dry type-method (the resin bonding type, the needle punching type, the stitch bonding type, the thermal bonding type, or the spun lace type-method), the wet type-method, the melt blow type method, the melting type-method (the spun bonding type-method).

The necessary conditions required of the surface protective material provided on the support body are that the surface protective material must be non-reactive with the resin, that it can be released from the resin component, and that it must be firm to some degree. As the surface protective material, a film made of polyethylene, polypropylene or the like, or a paper or a film treated with silicone, polytetrafluoroethylene (Teflon) or the like is used. The thickness thereof should desirably be from about 10 to about 5000 μm, more preferably from about 30 to about 50 μm.

The necessary conditions required of the material of the hermetically sealed container in which the main fixing body is accommodated are as follows: the material must be non-reactive with the resin and can be released from the resin, it must have neither moisture permeability nor air permeability, and it can be heat-sealed and manually torn open. For instance, a laminate body or structure composed of polyethylene/aluminium/polyester layers and having a thickness of about 80 μm can be used.

As the cushioning member, there can be used a sheet constructed in such a manner that a core material 8 is covered with a front surface material 9 and a rear material 10 as shown in FIG. 1*b*. The cushioning member should desirably have a length and a width necessary to surround the diseased part of a patient's body and a thickness of from about 3 to about 22 mm. Further, the cushioning member should desirably be made of a material in which rifts or slits can be formed as required. The necessary conditions required of the core material are that the core material must have elasticity, that it must be unyielding or must not break down, and that it must be air-permeable. The cushioning member is composed of, for instance, a polyurethane foamed material and should desirably have a thickness of from about 3 to about 20 mm, more preferably from about 5 to about 15 mm, and a foaming density of from about 12 to about 70 kg/m$^3$, preferably from about 16 to about 20 kg/m$^3$. The necessary conditions required of the front surface material are that it can bond to the resin and that it can also fasten to the hook portions of hook-and-loop fasteners. A particularly desirable material is, for instance, a pile fabric of polyamid (raising tricot fabric) and, more preferably, a pile fabric composed of polyamid threads of about 70 denier. The desirable conditions required of the rear surface material are that it should be moisture-absorptive, and that it should be air-permeable, for instance, a cotton pile of, for instance, 26 gauge, #40 and 150 g/m (120 cm in width) is desirable for the rear surface material. The provision of slits in the cushioning member is for ensuring that, by the slits, the cushioning member is divided into a plurality of areas, so that the fixing force obtained when the side ends of the outer surface of the cushioning member are joined together by use of the hook-and-loop fasteners can be independently varied in the respective areas. Whether the provision of such slits is necessary or not, or how many slits are to be formed can be determined as required.

The fixing member can be manufactured for instance in the following manner: a base material which is knitted to a large width is cut in the width direction into a predetermined shape in the state in which a portion in the longitudinal direction of said base material is coupled, and the thus processed base material is then treated in such a manner that, in a chamber maintained in a low-moisture environment, a curable resin with a viscosity of from about 18,000 to about 50,000 cps is applied to the base material with the interroll distance of a roll coater adjusted so that the amount of the curable resin applied may be from about 500 to about 2000 g/m², under the feeding of the curable resin to the roll coater. Thereafter, the thus treated base material is cut to a predetermined length, and both surfaces of the base material are covered with a covering material and a surface protective material which are previously cut to predetermined lengths, respectively. The resulting product is placed into the hermetically sealed container, substituting the atmosphere in the container with a nitrogen gas. In this case, it is alternatively possible to render the base material into a predetermined size by punching and applying the resin to it, and feeding the thus punched-out base material to the roll coater.

The cushioning member can be fabricated in such a manner that an adhesive is applied to both surfaces of the core material, and, to the respective surfaces thus treated, the front surface material and rear surface material are attached, and the whole is dried under pressure, after which the thus obtained product is cut to a predetermined size.

Effects Of The Invention

According to the present invention, the support body forms a flexible base material and is made to cure in the state in which it is directly conformed to the diseased part of a patient's body, so that the main fixing body can be made to accurately match the diseased part; and the cushioning member is directly wrapped or wound around the diseased part and fixed to the diseased part by use of hook-and-loop fasteners using the outer surface of the cushioning member as the loop portion of the fastener, and then, onto this cushioning member, the main fixing body is fixed by utilizing the curing of the curable resin thereof, so that even the main fixing body can also be fixed to the diseased part through the cushioning member itself without the necessity of using any means for fixing the main fixing member from outside; and in addition, since the cushioning member can be detachably mounted onto the diseased part by means of the hook-and-loop fasteners, the whole orthopaedic support can be very easily mounted onto the diseased part and demounted therefrom without the necessity of carrying out the complicated work of destroying the main fixing member or removing the means which fixes the main fixing member from outside. The main fixing member can be used over a long period of time until the diseased part is cured, and further, by adjusting the clamping force of the cushioning member by the hook-and-loop fasteners, the fixing force can be adjusted to a required value. Thus, the accurate forming of the orthopaedic support into a shape conformed to that of the diseased part, the mounting and demounting of the orthopaedic support during the period of a medical treatment, and the adjustment of the fixing force are very much facilitated, and at the same time, the so formed orthopaedic support is excellent from the economical point of view, too.

Thus, there has been shown and described an orthopaedic supporter which fulfills all of the objects and advantages set forth above. It will be apparent to those skilled in the art, however, that many changes, modifications, variations and other uses and applications for the subject invention are possible. All such changes, modifications, variations and other uses which do not depart from the spirit and scope of the invention are deemed to be covered by the invention, which is limited only by the claims which follow.

What is claimed is:

1. An orthopaedic supporter kit comprising:
    (a) a fixing member including a main fixing body hermetically enclosed within a moisture-impermeable container, said main fixing body being comprised of a support body made of a flexible base material impregnated with a curable resin which cures upon contact with water, a covering member which covers the outer surface of said support body and is bondable to the curable resin, and a separable surface protective member which covers the inner surface of said support body,
    (b) a cushioning member formed of a relatively elastic and bulky material in which slits can be formed,
    (c) hook-and-loop fasteners which can fasten to an outer surface of said cushioning member,
    wherein said cushioning member has an inner surface which can be directly applied to the diseased part of a patient's body, and the outer surface of said cushioning member includes opposite side end portions that can be coupled together by means of said hook-and-loop fasteners, and
    wherein said main fixing body can be taken out from within the moisture-impermeable container and contacted with water, then, the separable protective member is removed from the inner surface of the support body and the support body brought into contact with the outer surface of the cushioning member and, in this state, left to cure, whereby the support body, the covering member of the main fixing body and the cushioning member can be rendered into one integral structure that can be detachably fixed to the diseased part by means of said hook-and-loop fasteners.

2. The orthopaedic supporter kit of claim 1 wherein the curable resin includes at least a prepolymer, a catalyst, a stabilizer, a defoaming agent, and an anti-oxidant.

3. The orthopaedic supporter kit of claim 1 wherein the prepolymer is selected from the group consisting of a polyol and polyisocyanate.

4. The orthopaedic supporter kit of claim 2 wherein the prepolymer is a polyol selected from the group consisting of a polyethylene glycol, a polypropylene glycol, a polyester polyol, a polycaprolaction diol, a polyoxyethylenesorbitan ester, and an ethoxylated castor oil.

5. The orthopaedic supporter kit of claim 2 wherein the prepolymer is a polyisocyanate selected from the group consisting of 4,4'-diphenylmethane diisocyanate, methylene-bis(4-cyclohexyl isocyanate),5'-naphthalene diisocyanate, xylene diisocyanate, tolylene diisocyanate, and hexamethylene diisocyanate.

6. The orthopaedic supporter kit of claim 1 wherein the water curable resin has a viscosity of from about 18,000 to about 50,000 cps.

7. The orthopaedic supporter kit of claim 1 wherein the support body is made of a flexible base fabric material of fibers selected from the group consisting of natural fibers, artificial fibers, and a combination of natural fibers and artificial fibers.

8. The orthopaedic supporter kit of claim 1 wherein the support body is of knit construction.

9. The orthopaedic supporter kit of claim 8 wherein the knit is a three layered knit.

10. The orthopaedic supporter kit of claim 1 wherein the covering member is made from non-woven fabric.

11. The orthopaedic supporter kit of claim 1 wherein the cushioning member includes a polyurethane foam layer.

12. The orthopaedic supporter kit of claim 11 wherein the foam has a density of from about 12 to about 70 Kg/m³.

13. The orthopaedic supporter kit of claim 1 wherein slits are formed in said cushioning member at spaced locations along said opposite side end portions.

14. The orthopaedic supporter kit of claim 1 wherein said cushioning member is air-permeable.

15. The orthopaedic supporter kit of claim 1 wherein the outer surface of said cushioning member comprises a material capable of bonding to the curable resin and fastening to the hook portion of a hook and loop fastener.

16. The orthopaedic supporter kit of claim 15 wherein the outer surface material is a polyamide pile fabric.

17. The orthopaedic supporter kit of claim 1 wherein the inner surface of said cushioning member comprises a cotton pile fabric.

18. An orthopaedic supporter kit comprising:
   (a) a fixing member including a main fixing body enclosed within a moisture-impermeable container, said main fixing body being comprised of a support body made of a flexible base material impregnated with a water curable resin, the support body having an outer surface and an opposite inner surface, a covering member covering the outer surface of said support body and bondable to the curable resin, and a separable surface protective member which covers the inner surface of said support body.
   (b) a cushioning member separate from the fixing member formed of a relatively elastic and bulky material, the cushioning member having an outer surface, an opposite inner surface, and opposite side end portions, said cushioning member being adapted to be positioned around a diseased part of a patient's body and conformed to the shape of the diseased part with the inner surface of said cushioning member directly applied to the diseased part and the opposite side end portions positioned in adjacent relation so as to be capable of being coupled together,
   (c) fasteners for adjustably coupling together the side end portions of said cushioning member, and
   wherein said main fixing body can be removed from within the moisture-impermeable container and contacted with water, then, the separable protective member is removed from the inner surface of the support body and the inner surface of the support body brought into contact with the outer surface of the cushioning member and, in this state, left to cure, whereby the support body, the covering member of the main fixing body and the cushioning member can be rendered into one integral structure which can be detachably fixed to the diseased part by means of said fasteners.

19. The orthopaedic supporter kit of claim 18 wherein at least one side end portion of the cushioning member is slitted at spaced intervals to form discrete side end portions, and the discrete side end portions are independently adjustably coupleable to the opposite side end portion.

20. An orthopaedic supporter kit comprising:
   (a) a fixing member including a main fixing body comprised of a support body made of a flexible base material impregnated with a water curable resin, the support body having an outer surface and an opposite inner surface, and a separable surface protective member which covers the inner surface of said support body,
   (b) a separate cushioning member formed of a relatively elastic cushioning material, the cushioning member having an outer surface, an opposite inner surface, and opposite side end portions extending along opposite edges of said outer surface, said cushioning member being mountable around a diseased part of a patient's body with the inner surface of the cushioning member in contact with the diseased part such that the cushioning member is conformed to the shape of the diseased part and the opposite side end portions are positioned so as to be capable of being coupled together,
   (c) fasteners for adjustably coupling together the side end portions of said cushioning member, wherein the support body of said main fixing body can be contacted with water, then, the separable protective member is removed from the inner surface of the support body and the main fixing body mounted on the cushioning member with the inner surface of the support body in contact with the outer surface of the cushioning member and, in this state, left to cure, whereby the main fixing body and cushioning member are rendered into an integral structure that can be detachably fixed to the diseased part by means of said fasteners.

* * * * *

UNITED STATES PATENT AND TRADEMARK OFFICE
CERTIFICATE OF CORRECTION

PATENT NO. : 5,577,999
DATED : November 26, 1996
INVENTOR(S) : Takayuki Sekine, et. al.

It is certified that error appears in the above-indentified patent and that said Letters Patent is hereby corrected as shown below:

Column 9, line 20, "." after body should be --,--.

Signed and Sealed this

Eleventh Day of March, 1997

Attest:

BRUCE LEHMAN

Attesting Officer

Commissioner of Patents and Trademarks